United States Patent [19]

Mirabelli

[11] Patent Number: 5,037,978
[45] Date of Patent: Aug. 6, 1991

[54] HAFNIUM-CATALYZED TRANSESTERIFICATION

[75] Inventor: Mario G. L. Mirabelli, Horsham, Pa.

[73] Assignee: Rohm and Haas Company, Philadelphia, Pa.

[21] Appl. No.: 492,528

[22] Filed: Mar. 12, 1990

[51] Int. Cl.$^5$ ............... C07D 265/30; C07D 295/18; C07D 211/30; C07C 67/03

[52] U.S. Cl. .................... 544/171; 546/248; 548/235; 548/341; 548/342; 558/444; 560/217

[58] Field of Search .............. 544/171; 546/248; 548/341, 342, 235; 558/444; 560/217

[56] References Cited

U.S. PATENT DOCUMENTS

| | | | |
|---|---|---|---|
| 4,202,990 | 5/1980 | Murakami et al. | 560/217 |
| 4,594,439 | 6/1986 | Katsuki et al. | 560/218 |
| 4,609,745 | 9/1986 | Dieter et al. | 546/106 |
| 4,609,755 | 9/1986 | Farrar | 560/217 |
| 4,777,265 | 10/1988 | Franz et al. | 546/106 |

FOREIGN PATENT DOCUMENTS 2194914 7/1987 United Kingdom .

*Primary Examiner*—Johann Richter
*Attorney, Agent, or Firm*—Terence P. Strobaugh; Lowell H. McCarter

[57] ABSTRACT

An ester of a carboxylic acid is prepared via a transesterification reaction which comprises reacting a lower alkyl ester of carboxylic acid with a higher alkyl alcohol in the presence of a catalyst consisting of a hafnium chelate derived from hafnium tetrachloride, bis(alkoxide)hafnium dichlorides, or hafnium tetraalkoxides in the presence of 1,3-dicarbonyl compounds.

10 Claims, No Drawings

HAFNIUM-CATALYZED TRANSESTERIFICATION

FIELD OF THE INVENTION

This invention relates to an improved process for the production of esters, particularly unsaturated carboxylic esters, by catalytic transesterification reaction. In particular, the invention relates to an improved process for production of acrylate and methacrylate esters using 1,3-dicarbonyl chelates of hafnium as catalysts in the transesterification reaction.

BACKGROUND OF THE INVENTION

Esters of saturated and unsaturated carboxylic acids can be produced by ester exchange, or transesterification, reactions. Transesterification reactions normally are carried out in the presence of a catalyst to accelerate the reaction desired. In the past, typical catalysts included materials such as sulfuric acid, toluenesulfonic acid, alkali metal alkoxides, or metal alkoxides such as those of titanium or aluminum. However, these catalysts suffer from a variety of drawbacks, especially with the esters of unsaturated carboxylic acids. For example, if strong mineral acids such as sulfuric acid or methanesulfonic acid are used, the reaction rates are generally quite slow and the formation of the transester product is normally accompanied by the formation of high concentrations of side-products. These by-products not only include Michael-addition products (addition of alcohol to C=C double bond) but also substantial amounts of polymeric products. In addition, primary or secondary alcohols may be dehydrated by strong acids, thus contaminating the product monomer with olefins derived from the starting alcohols.

On the other hand, alkali metal alkoxide catalysts (for example, sodium methoxide or potassium tert-butoxide), not only promote undesireable side reactions, but are also deactivated by the presence of water in the reaction solution. Therefore, it is necessary to continuously add catalyst to the reaction mixture. Furthermore, the catalyst must then be removed to avoid alkoxide-promoted polymerization or degradation during distillation or other thermal treatment of the products, especially if the products are unsaturated esters such as acrylic esters. Aluminum and titanium alkoxides also suffer from many of these same drawbacks. Titanate catalysts are especially sensitive to water (generally losing activity in mixtures containing greater than 500 ppm water), thus necessitating the same need to add more catalyst to the reaction. In addition, applications that require the catalyst to remain in solution (for example, when a monomeric product is not distilled) are hampered by the subsequent precipitation of hydroxides and oxides from the resultant product upon exposure to traces of water. Because of these problems with conventional catalysts, a need exists for an improved transesterification catalyst of high activity and selectivity and reduced sensitivity to water.

Some steps toward meeting this need have been taken in the art. For example, the utilization of titanium (Ti) and zirconium (Zr) transition metal complexes to catalyze transesterification reactions has been reported. Thus, as described in U.S. Pat. No. 4,202,990, various alcohols are treated with (meth)acrylic esters in the presence of a zirconium acetylacetonate catalyst to produce transester products in high yields. Also, U.S. Pat. No. 4,609,755 describes the activation of Ti/Zr alkoxides by Mg, Ca, and Ba alkoxides for ester interchange of (meth)acrylic esters. Some of the deficiencies mentioned above still exist, however. I have now found that it is possible to achieve very high yield of transesterified ester products by reaction of a lower alkyl ester with an appropriate alcohol in the presence of a hafnium(IV) 1,3-dicarbonyl complex, which complex shows unexpectedly high activity without the subsequent precipitation or insolubility problems associated with the prior art catalysts.

SUMMARY OF THE INVENTION

This invention is directed to a general catalyst of high activity and selectivity for the production of a variety of esters, particularly acrylate and methacylate-based esters, by the transesterification reaction. This objective is achieved by reacting a lower alkyl ester of a saturated or unsaturated, typically, a 3 to 4 carbon atom carboxylic acid with a higher alcohol than the alcohol fragment of the lower alkyl ester in the presence of a catalyst consisting of chelate compounds of hafnium(IV) and 1,3-dicarbonyl compounds, by an ester exchange reaction. The hafnium chelates are prepared and isolated from readily available starting materials such as hafnium tetrachloride or may be prepared from similar starting materials within the reaction medium without the need for isolation (in-situ preparation).

DETAILED DESCRIPTION OF THE INVENTION

The reaction related to the present invention is described as follows, using unsaturated esters as illustrative starting materials:

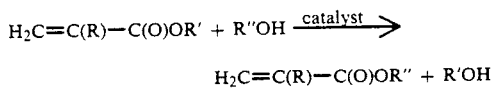

$$H_2C=C(R)-C(O)OR' + R''OH \xrightarrow{catalyst}$$

$$H_2C=C(R)-C(O)OR'' + R'OH$$

In the process, suitable starting esters include the acrylate or methacrylate esters, where R is H or $CH_3$, and R' is lower alkyl of from 1 to 4 carbon atoms, and preferably 1 or 2 carbon atoms; a suitable starting alcohol is represented by the formula R"OH, where R" is alkyl or cycloalkyl, for example lower alkyl and cyclo lower alkyl containing from 3 to 20 carbon atoms. R" may also be alkoxyalkyl, alkylpolyalkoxyalkyl, alkylphenoxyalkyl, alkylpolyphenoxyalkyl, phenylalkyl, alkylphenylalkyl, alkylmorpholinoalkyl, alkylpiperidinoalkyl, haloalkyl, cyanoalkyl, alkylthioalkyl, alkylimidazolidinones, alkyl oxazolidines, hydroxy alkyl such as hydroxyethyl, hydroxybutyl and the like, for example those derived from ethylene glycol, butanediol, polyoxyethyleneols, and the like. Preferred are those alcohols wherein the alkyl portions described in the above compounds is lower alkyl having from 2 to 20 carbon atoms. Examples of alcohols include butanol, pentanol, isodecyl, lauryl, cetyl, stearyl, alkyl ether of polyoxyethylene, 2-N-oxazolidinyl)ethyl, 2(N-morpholino)ethyl, dicyclopentenyloxyethyl, and the like.

The general requirements for the suitability of alcohol for the transesterification reaction are that it is of higher normal boiling point than the lower alkyl alcohol being replaced (R'OH) and that it is stable to the relatively mild conditions of the reaction. Alcohols containing relatively high water contents (>1000 ppm) are dehydrated by conventional methods before use, e.g. as by azeotropic dehydration, although the hafnium catalysts of this invention are found to readily tolerate alcohol water levels of 200-500 ppm with no significant decrease in activity, in contrast to many other catalysts in the art.

The catalyst of the present invention consists of chelated compounds of hafnium and/or mixed chelated alkoxide complexes of hafnium represented by the following general formula (I):

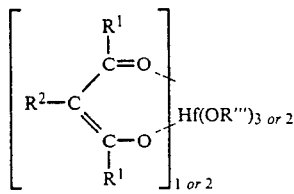

where $R^1$ is $C_1$-$C_4$ alkyl or phenyl, $R^2$ is hydrogen, $C_1$-$C_4$ alkyl, phenyl or substituted phenyl such as p-methylphenyl, p-hydroxyphenyl, and the like, and $R''''$ is the same or different radical selected from $R'$ and $R''$ as defined above. The $OR''''$ substituent may be a combination of alkoxide groups, or "ligands" in chelate terminology, composed of one or more of the following: a precursor lower alkoxide used in a prior generation of a chelate; the alkoxide formed from the alcohol having a carbon content higher than the alkyl group of the lower alkyl ester, that is, the transesterifying alcohol, $R''OH$; or the alkoxide formed from the lower alcohol of the lower alkyl ester, $R'OH$. (Structure (I) is presented as a likely and reasonably hypothesized structure of the hafnium chelate alkoxide complex.)

Suitable chelate compounds of hafnium include for example the acetylacetonate, 2,4-hexanedionate, 3,5heptanedionate, 3-phenylacetoacetonate, 2,2,6,6 tetramethyl-3,5-heptanedionate, or 1,3-diphenylacetonate.

The formula of a preferred hafnium chelate alkoxide catalyst is represented by formula II, in which the bis-acetylacetonate chelate is complexed with two alkoxide ligands, $OR''''$, as defined above:

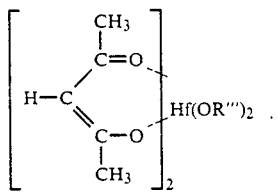

Hafnium(IV) acetylacetonate, formula III, is also highly effective in catalyzing the transesterification process of this invention.

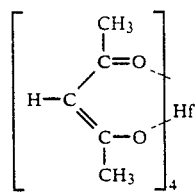

The catalysts may be prepared by conventional methods well known in the art; for example, hafnium(IV) acetylacetonate may be prepared by the reaction of hafnium tetrachloride with 2,4-pentanedione and triethylamine in toluene solvent. The solid catalyst is purified and isolated by recrystallization from a 50:50 by weight toluene:hexane solvent mixture, dried, and characterized by its melting point and proton nuclear magnetic resonance spectrum as the tetra acetylacetonate of hafnium. Alternatively, hafnium chelates may be generated in-situ in transesterification mixtures or solutions by mixing hafnium tetrachloride with triakylamines and the appropriate dione, or bis(alkoxide)hafnium dichloride with triakylamines and the appropriate dione. The catalyst also is generated by mixing hafnium alkoxide complexes in the presence of free dione in the reaction mixture. It is a key aspect of this invention that in the absence of one or more diones, compounds well known to form chelate complexes with metal ions, the hafnium alkoxide complexes were not effective in transesterification catalysis.

In the preparation of the hafnium catalyst in-situ from the bis or tetrachloride, one molar equivalent of trialkylamine per mole of chloride was found most effective. Preferred trialkylamines included those with alkyl groups containing from one to four carbon atoms, although higher alkyl groups also can be used.

In the preparation of the hafnium catalyst in-situ from the bis or tetrachloride, or from the tetraalkoxide directly, the most effective ranges of the added free dione were from one to four molar equivalents of dione per mole of hafnium. The alkoxides found to be effective were those composed of from one to four carbon atoms, with ethyl and tertiary-butyl groups most effective.

In this process, the starting (meth)acrylic ester may be used as an azeotroping solvent to facilitate removal of the product alcohol and to drive the reaction to completion. Other suitable solvents such as hexane, cyclohexane and heptane also may be used for these purposes.

The hafnium catalysts of this invention are used in amounts of from about 0.01 to about 5.0 mol % based on the initial charge of alcohol. Larger amounts of catalyst may be used but are not usually necessary. In the specific use of hafnium (IV) acetylacetonate, amounts of from about 0.05 to about 0.50 mol % are effective and preferred. Catalyst typically is present at the beginning of reactant combination and remains present throughout the reaction period, whether added neat or as prepared in-situ.

The initial mole ratio of saturated, aromatic, or unsaturated (for example, (meth)acrylic) ester to alcohol generally is 2:1 to 10:1, and is preferably 2:1 to 5:1.

The reaction is carried out under atmospheric or reduced pressure conditions. Suitable reaction temperatures range from about 50° C. to about 140° C., more typically from about 80° C. to about 120° C. The starting materials normally are brought to reflux in the presence of the catalyst while the product alcohol is azeotroped from the system, facilitated by excess of the starting ester. On completion of the reaction the catalyst may be removed, if desired, from the product by treating the product mixture with activated carbon, neutral alumina, silica, silica/alumina, and the like. A particular advantage in using hafnium acetylacetonate and other related chelate catalysts is that it is usually not necessary to remove them when the reaction is completed, since their presence does not cause detrimental effects on subsequent polymerization of unsaturated products or in many other applications of saturated, aromatic, or unsaturated products.

When polymerizable materials are used or produced in the present invention, polymerization inhibitors are beneficial in the reaction mixtures. Examples of such materials include hydroquinone, hydroquinone monomethylether, phenothiazine, diethylhydroxylamine, and di-tert-butylcatechol. In addition, oxygen also may be found beneficial in inhibiting polymerization in the presence of inhibitors and is introduced into the reaction system, often in the form of air, in amounts such that the gas phase above the reaction mixture remains below the explosion limit.

Having described the invention in general terms, more specific examples are provided below for purposes of illustrating the present invention.

EXAMPLE 1

Isodecyl Methacrylate (IDMA)

Four hundred seventy four grams (3.0 moles) of isodecyl alcohol, 750 g (7.5 moles) of methyl methacrylate (MMA), 1.75 g (3.0 millimol) of hafnium actylacetonate, and 50 mg diethylhydroxylamine and 25 mg phenothiazine free radical polymerization inhibitors, are added to a 3 liter flask equipped with an agitator, thermometer, and a 10-plate Oldershaw fractional distillation column. The mixture was heated to reflux at atmospheric pressure while an azeotropic mixture of MMA and methanol was removed from the upper part of the fractionating column. The reaction was continued in this manner for approximately 90 minutes while the temperature at the top of the column was 65°-67° C. and the temperature in the pot was 106°-124° C. Excess MMA was removed under vacuum and the resulting IDMA was isolated (660 grams, 99.0% yield) and analyzed. Gas-liquid chromatographic (GLC) analysis showed >99.9% conversion of isodecanol to IDMA of 99.8% purity.

EXAMPLE 2

Cetyl Methacrylate (CEMA)

An example utilizing a mixture of higher alcohols was performed by adding 600 g (ca. 2.3 moles) of a mixture of 16-20-carbon alcohols (primarily cetyl alcohol), 920 g (9.2 moles) of MMA, 1.32 g (2.3 mmol) of hafnium acetylacetonate, 60 mg diethylhydroxylamine and 30 mg of phenothiazine inhibitors, to a 3 liter flask as described above. The solution was heated at reflux (atmospheric pressure) for approximately 2 hours while removing the MMA/MeOH azeotrope. The temperature at the top of the column was 65°-66° C. and the temperature in the pot was 108°-117° C. The MMA was removed in vacuo and the resulting CEMA was isolated (750 g, 98.8% yield based on alcohol) and analyzed. GLC analysis showed 99.9% conversion of alcohol to CEMA of approximately 97.5% purity.

EXAMPLE 3

Butyl Methacrylate via In-Situ Catalyst Generation

An example utilizing an in-situ hafnium catalyst was performed by adding 20.0 g (274 mmol) n-butanol, 135 g (1.35 mole) MMA, 20 mg phenothiazine to a 300 ml round bottom flask equipped with an agitator, thermometer, and Vigreux fractional distillation column. The solution was dehydrated by refluxing the mixture at atmospheric pressure and removing water via a MMA/water azeotrope. The mixture was then cooled to 0° C. (ice bath) where 1.63 g (16.1 mmol) triethylamine, 1.0 g (10.0 mmol) 2,4-pentanedione, and 870 mg (2.72 mmol) hafnium tetrachloride were added to the solution. The catalyzed mixture was heated to reflux at 1 atm. pressure while azetropic mixture of MMA and MeOH was removed from the upper part of the fractionating column. The reaction was continued in this manner for approximately 2 hours while the temperature at the top of the column was 65°-67° C. and the temperature in the pot was 97°-112° C. Analysis of the reaction mixture by gas-liquid chromatographic analysis showed greater than 99% conversion of the n-butanol to n-butyl methacrylate.

EXAMPLE 4

Butyl Acrylate

One hundred forty eight grams (2.0 moles) of n-butanol, 516 g (6.0 moles) methyl acrylate, 1.15 g hafnium acetylacetonate, 0.10 g of MEHQ inhibitor, 0.1 g phenothiazine, and 0.10 g diethylhydroxylamine were added to a 2 liter flask equipped as described in Example 3. The solution was heated at reflux (atmospheric pressure) while an azeotropic mixture of methyl acrylate and methanol was removed from the top of the column. The reaction was continued in this manner for 2 hours while the temperature at the top of the column was 62°-64° C. and the temperature in the reaction vessel was 82°-97° C. GLC analysis of the reaction mixture showed >99% conversion of the n-butanol to butyl acrylate.

EXAMPLE 5

Polyethoxyalkyl Methacrylate

A catalyzed transesterification employing a polyethoxylated ether alcohol was run. Thus, 208 g (0.173 mole) of the lauryl ether of polyoxyethylene of polymerization degree 23 (polyoxyethylene 23, lauryl ether), 87 g (0.87 mole) MMA, 2.00 g (3.50 mmol) hafnium acetylacetonate, and 210 mg of MEHQ were added to a 500 ml flask equipped with an agitator, thermometer, and fractional distillation column. The mixture was heated at reflux under reduced pressure (400 mm Hg) while the MMA/method azetrope was removed at the top of the column. The reaction was essentially complete after two hours. The temperature at the top of the column during the reaction was 48°-50° C. while the temperature in the reaction vessel was 105°-115° C. Analysis showed that 99% of the starting ether alcohol had been converted to the transesterified product.

EXAMPLE 6

Butyl Benzoate

The preparation of butyl benzoate was performed by adding 272 g (2.0 moles) of methyl benzoate, 167 g (2.25 moles) n-butanol, 1.0 g (2.0 millimole) of hafnium acetylacetonate, and 90 g of hexane solvent to a 1 liter flask equipped with an agitator, thermometer, 5-plate Oldershaw fractional distillation column, and a Dean and Stark trap. The solution was heated to atmospheric reflux while an azeotropic mixture of hexane and methanol was removed at the top of the column. The reaction was continued in this manner for approximately 8 hrs while the temperature in the pot was 84°-97° C. The mixture was vacuum distilled to yield 339 g (1.90 mole, 95.2% isolated yield) of butyl benzoate. The product was characterized by proton NMR.

The foregoing description of the invention are set forth only by way of illustration. As will be readily apparent to those skilled in the art, other variations and modifications can readily be employed without departing from the spirit and scope of the invention, which is described above and embodied in the following claims.

I claim:

1. A transesterification process which comprises treating a lower alkyl ester of a carboxylic acid of the formula:

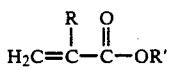

wherein R is H or CH$_3$, and R' is alkyl, with an alcohol of the formula R"OH wherein R" is alkyl, cycloalkyl, alkoxyalkyl, alkylpolyalkoxyalkyl, alkylphenoxyalkyl, alkylpolyphenoxyalkyl, phenylalkyl, alkylphenylalkyl, alkylmorpholinoalkyl, alkylpiperdinoalklyl, haloalkyl, cyanoalkyl, alkylthioalkyl, alkylimidazolidinones, alkyloxozolidines or hydroxyalkyl with the proviso that the alcohol has a carbon content higher than the alkyl group of the carboxylic acid ester with a hafnium (IV) chelate.

2. The process of claim 1 wherein the hafnium (IV) chelate catalyst has the formula:

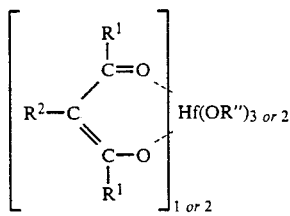

wherein R$^1$ is C$_1$–C$_4$ alkyl of phenyl, R$^2$ is hydrogen, C$_1$–C$_4$ alkyl, phenyl or substituted phenyl and R"" is alkyl, cycloalkyl, alkoxyalkyl, alkylpolyalkoxyalkyl, alkylphenoxyalkyl, alkylpolyphenoxyalkyl, phenylalkyl, alkylphenylalkyl, alkylmorpholinoalkyl, alkylpiperdinoalkyl, haloalkyl, cyanoalkyl, alkylthioalkyl, imidazolidinylalkyl, oxazolidinylalkyl or hydroxyalkyl.

3. The process of claim 2 wherein the alcohol having a carbon content higher than the alkyl group of the lower ester has the formula: R"OH wherein R" is lower alkyl or cyclo lower alkyl, lower alkoxy lower alkyl, lower alkyl polyalkoxy lower alkyl, lower alkylpolyphenoxy lower alkyl, phenyl lower alkyl, lower alkylphenyl alkyl, lower alkylmorpholino lower alkyl, lower alkylpiperidino lower alkyl, halo lower alkyl, cyano lower alkyl, lower alkylthio lower alkyl, lower alkyl imidazolidinyl, lower alkyl oxazolidinyl, or hydroxy lower alkyl.

4. The process of claim 1 wherein the mole ratio of the catalyst to the higher alcohol is in the range of from about 0.0001 to about 0.10:1.

5. The process of claim 4 wherein R$^1$ is C$_1$–C$_4$alkyl or phenyl, R$^2$ is hydrogen, C$_1$–C$_4$alkyl, phenyl or substituted phenyl, and R"" is lower alkyl or cyclo lower alkyl, lower alkoxy lower alkyl, lower alkyl polyalkoxy lower alkyl, lower alkylpolphenoxy lower alkyl, phenyl lower alkyl, lower alkylphenyl alkyl, lower alkylmorpholino lower alkyl, lower alkylpiperidino lower alkyl, halo lower alkyl, cyano lower alkyl, lower alkylthio lower alkyl, lower alkyl imidazolidinyl, lower alkyl oxazolidinyl, or hydroxy lower alkyl.

6. The process of claim 5 wherein R$^1$ is C$_1$–C$_4$alkyl, R$^2$ is hydrogen, C$_1$–C$_4$alkyl, or phenyl, and R"" is lower alkyl or cyclo lower alkyl, lower alkoxy lower alkyl, lower alkyl polyalkoxy lower alkyl, lower alkylpolyphenoxy lower alkyl, phenyl lower alkyl, lower alkylphenyl alkyl, lower alkylmorpholino lower alkyl, lower alkylpiperidino lower alkyl, halo lower alkyl, cyano lower alkyl, lower alkylthio lower alkyl, lower alkyl imidazolidinyl, lower alkyl oxazolidinyl, or hydroxy lower alkyl.

7. The process of claim 6 wherein R$^1$ is C$_1$–C$_4$alkyl, R$^2$ is hydrogen or C$_1$–C$_4$alkyl, and R"" is lower alkyl, lower alkoxy lower alkyl, lower alkyl polyalkoxy lower alkyl, lower alkylpolyphenoxy lower alkyl, phenyl lower alkyl, lower alkylphenyl alkyl, lower alkylmorpholino lower alkyl, lower alkylpiperidino lower alkyl, halo lower alkyl, cyano lower alkyl, lower alkylthio lower alkyl, lower alkyl imidazolidinyl, lower alkyl oxazolidinyl, or hydroxy lower alkyl.

8. The process of claim 1 wherein the catalyst is hafnium acetylacetonate.

9. The process of claim 1 wherein the lower alkylester of a carboxylic acid is methyl acrylate, ethyl acrylate, methyl methacrylate, or ethyl methacrylate.

10. The process of claim 9 wherein the mole ratio of hafnium cat- alyst to the alcohol is in the range of from about 0.0002 to about 0.05:1.

* * * * *